United States Patent [19]

Hultquist

[11] 4,356,196

[45] Oct. 26, 1982

[54] PROCESS FOR TREATING ALFALFA AND OTHER CELLULOSIC AGRICULTURAL CROPS

[76] Inventor: Joe H. Hultquist, 616 Dockside Cove, Hastings, Nebr. 68901

[21] Appl. No.: 198,712

[22] Filed: Oct. 20, 1980

[51] Int. Cl.$^3$ .............................................. A23K 1/22
[52] U.S. Cl. .................................... 426/69; 426/635; 426/807
[58] Field of Search ................ 426/69, 635, 636, 807, 426/447, 449

[56] References Cited

U.S. PATENT DOCUMENTS

| | | | |
|---|---|---|---|
| Re. 22,477 | 5/1944 | Millar | 426/69 |
| 2,789,906 | 4/1957 | Zick | 426/69 |
| 2,810,649 | 10/1957 | Bonnell | 426/635 |
| 3,259,501 | 7/1966 | Ulrey | 426/69 |
| 3,667,961 | 6/1972 | Algeo | 426/447 |

OTHER PUBLICATIONS

Moore et al., J. Agr. Food Chem. vol. 20, No. 6, 1972, pp. 1173-1175.
Saenger et al., "Anhydrous Ammonia Treatment of Corn Stalks," pp. 111-116, Beef Cattle Day, Purdue University, Mar. 14, 1980.
Baker et al., Cellulose Technology Research, pp. 75-87, ACS Symposium Series 10, Am. Chem. Society, Wash., DC (1975).

*Primary Examiner*—Raymond N. Jones
*Assistant Examiner*—George C. Yeung
*Attorney, Agent, or Firm*—Kokjer, Kircher, Bradley, Wharton, Bowman & Johnson

[57] ABSTRACT

Alfalfa and other cellulosic agricultural crops and crop derivatives are treated with ammonia under pressure to increase the true protein availability and the cellulose digestibility. The materials can be evacuated from the reaction vessel either gradually or explosively, with explosive evacuation providing a dust free product having a greener color. The ammonia is recycled by recovering it and recompressing it for reuse in treating an additional quantity of crop.

4 Claims, No Drawings

PROCESS FOR TREATING ALFALFA AND OTHER CELLULOSIC AGRICULTURAL CROPS

BACKGROUND OF THE INVENTION

This invention relates to a process involving the treatment of alfalfa and other crops with ammonia under pressure in order to enhance the true protein availability and the cellulose digestibility of the crop.

Alfalfa is universally recognized as an important ingredient in livestock feed rations, due primarily to its high quality protein content and the other nutrients it furnishes. Even so, the uses of alfalfa are limited by its high fiber content (lignin and cellulose) and its low energy content as compared to its protein concentration. The more mature plants and those having a high stem to leaf ratio provide greater cellulose content but lower cellulose digestibility by enzymes. The available data relating to alfalfa composition indicate that crude protein is present in the range of 13% to 22%, lignin is present in the range of 5% to 11% and cellulose is present in the range of 18% to 43%.

If the available protein and energy content of alfalfa could be upgraded in an economical manner, its value as livestock feed would be improved and additional important benefits would result. For example, economic improvement of the alfalfa product would make it feasible to place alfalfa in the formerly common crop rotation systems. Alfalfa has advantages as a crop in several respects, most notably due to its relatively high yield of protein per acre and its relatively low fossil fuel requirements. Alfalfa produces at least twice as much protein per acre as other common crops, and its fossil fuel requirements are reduced both directly in the fuel required per ton of crop production and indirectly in reduced needs for equipment, fertilizer and pesticide. Approximately 150 to 200 pounds of nitrogen per acre is placed in the soil by alfalfa after two or three years of stand life, and the nitrogen is in forms which last longer than chemical fertilizers and which are less likely to contaminate ground water or cause other environmental problems. When alfalfa is included in the crop rotation, weed control and pest control measures are greatly facilitated. Consequently, the application of chemicals is reduced significantly, and both economic and environmental benefits are obtained. In addition, alfalfa achieves soil erosion control because it is a perennial crop that remains approximately five years without tillage.

Various approaches have been taken in efforts to improve the feed value of alfalfa. For example, the feed value per ton can be enhanced by harvesting the plant at early stages of maturity. However, the additional harvesting operations that are required, the lower annual crop yield and the reduced plant hardiness combine to render this approach impractical. Additionally, the metabolizable energy value of the alfalfa remains low even when the early harvesting technique is used.

Leaf protein concentrate developers have employed various techniques in attempts to achieve their goal of improving the protein to fiber situation in alfalfa. However, the mechanical methods that have been devised recover only about 50% of the total plant protein in the concentrate product. The balance remains as a low protein, high fiber pressed cake. The advantages of obtaining the protein concentrate are thus offset at least partially by the low value of the highly fibrous residue.

The technical literature indicates that attempts have been made to use ammonia to alter the cellulose structure. For example, exposure of alfalfa, wheat and rice straw to ammonia water at atmospheric pressure for 30 days has been found to improve the digestibility of the fiber. Exposure of orchardgrass bales to gaseous anhydrous ammonia at atmospheric pressure for a period of seven weeks, followed by three days of aeration, similarly improves the dry matter digestibility and crude protein content. However, in both cases, the time periods required for treatment of the hay are so lengthy as to make the processes impractical from a commercial standpoint. Other types of techniques that have been proposed for alteration of the cellulose structure are equally time consuming, are characterized by undue energy consumption such as is involved in ball milling, or use highly toxic materials or materials which are difficult to recover for reuse.

As reported by Andrew J. Baker and Merrill A. Millett in an article entitled "Wood and Wood-based Residues in Animal Feeds," published in Cellulose Technology Research, Albin F. Turback, ed., ACS Symposium Series 10, American Chemical Society, Washington, DC (1975), sawdust from aspen trees has been treated with anhydrous ammonia under pressure. Although an appreciable increase in the digestibility of the aspen wood was observed, similarly successful results were not obtained with other types of wood, and the accepted conclusion was reached that aspen is unique in its digestibility response to ammoniation. This process is also characterized by excessive cost in that all of the ammonia is consumed and there is no effort made to recover any of the ammonia used in the treatment.

Techniques used in the production of alcohol from cellulosic materials involve the use of acids or basic substances to break or otherwise alter the lignin-cellulose bonds. A significant problem arising from this type of process is that the acid or base which is employed can break down the sugar as well as the cellulose. As a result, useful materials are destroyed and the glucose yield suffers accordingly. Furthermore, conventional processes involve fine grinding or ball milling operations which add significantly to the overall costs.

SUMMARY OF THE INVENTION

The present invention has, as its primary goal, the provision of an economical process for treating alfalfa and other agricultural crops and crop derivatives in a manner to enhance the protein availability and the digestibility of the cellulose. In accordance with the invention, ground alfalfa is exposed for a short time period to liquid or gaseous anhydrous ammonia under pressure. Following completion of the ammonia treatment, decompression can be carried out either gradually or in a rapid, explosive manner, depending upon the final product requirements. Explosive decompression through an orifice yields a nearly dust free product having a much more attractive, greener appearance, although both the protein availability and cellulose alteration are similar for the exploded and the gradually decompressed material.

Alfalfa treated by this process is approximately doubled in its cellulose digestibility as compared to untreated alfalfa, and its available true protein is increased by approximately 65% with a similar gain in crude protein. The product can be used as a mid-protein livestock feed with higher available energy or alternatively as a highly productive ethanol production feedstock providing protein concentrate yields that are generally greater than are obtained with mechanical extraction of fresh alfalfa juice.

More than 95% of the ammonia administered in the treatment process is available for recovery, and the recovered ammonia is preferably recycled to enhance the economy of the process. In a preferred form of the invention, the ammonia is recovered after it and the treated alfalfa have been decompressed to an intermediate pressure which is below the treatment pressure but above atmospheric pressure. Consequently, the pressure of the recycled ammonia must be raised only from the intermediate pressure to the treatment pressure rather than from atmospheric pressure to the treatment pressure. Thus, both the ammonia requirements and the pumping requirements are reduced significantly.

The glucose production yields obtained by the invention approach the theoretical maximum yields and are double the yields obtained from untreated alfalfa. The glucose can be used for alcohol production concurrent with the manufacturing of high protein concentrates, or the treated alfalfa can be used as a higher energy, mid-protein alfalfa feed for livestock.

Another significant advantage of the treatment process is that either fresh alfalfa or sun cured alfalfa hay can be used, thus permitting operation on a twelve month, non-seasonal basis without altering the prevailing techniques used in the harvesting of alfalfa. Also, the reaction time is relatively short so that there is the potential for continuous processing in order to achieve large scale commercial economies. The commercial potential is further improved due to the nearly complete recovery of the ammonia and its availability for recycling. Since alfalfa and other agricultural crops are presently harvested and collected by well developed techniques, there is no need to establish new collection techniques as would be necessary with another type of biomass.

DETAILED DESCRIPTION OF THE INVENTION

The present invention involves improving the available protein and available energy content of alfalfa and other agricultural crops and crop derivatives by applying ammonia to the crop under pressure. The ammonia is nearly anhydrous and can be applied in either the liquid or gas state. In the case of alfalfa, either sun cured or freshly harvested alfalfa hay can be used, and there are thus no seasonal restrictions on the process. Good results are obtained under normal conditions with the alfalfa hay ground to a 1/16 inch to ½ inch grind, and expensive ball milling or fine grinding operations are not necessary. Under some conditions, it is expected that no grinding at all will be necessary.

The quantity of ammonia applied to the crop can vary within a broad range. When liquid ammonia is applied to alfalfa, the practical operating range appears to be about ½ to 2 parts by weight ammonia per one part by weight alfalfa. Gaseous ammonia can be applied to the maximum pressure exerted by a supply tank containing some ammonia in the liquid state. The ammonia must be applied at a sufficient rate to penetrate the alfalfa if it is to effectively react therewith. The exposure time required to achieve good results varies with the condition of the crop, but from one minute to one hour covers the general operating range under normal conditions. With the equipment presently available to carry out the treatment, the exposure time that is most practical is about thirty minutes.

The temperature and pressure conditions necessary for successful results likewise vary depending upon the crop condition and the environmental conditions. However, the treatment pressure must be above atmospheric pressure and, with relatively low temperatures, good results can be obtained with pressures as low as two atmospheres. The practical pressure range for the treatment is from about two atmospheres to about 40 atmospheres. The practical temperature range is from about 10° C. to about 85° C. under most conditions. With mature, sun cured ground alfalfa hay, particularly good results are achieved in a temperature range of 20° C. to 30° C. and a pressure range of 145 psig to 165 psig for liquid ammonia and 70 psig to 125 psig for gaseous ammonia. As previously indicated, significant benefits are obtained at pressures as low as two atmospheres and lower temperatures.

The treatment process is carried out rapidly enough that it can be employed economically in a continuous system as well as on a batch basis. In the batch system, the pressure vessel that contains the materials remains sealed for the duration of the treatment. In the continuous system, the materials are continuously fed into the vessel and evacuated therefrom. The rate of entry of materials into the pressure vessel and their evacuation must be carefully controlled to maintain the appropriate pressure and flow rate.

The crop and ammonia can be evacuated from the pressure vessel either gradually or explosively upon elapse of the treatment period. Explosive evacuation can be effected by abruptly opening an exit orifice located beneath the alfalfa level in the vessel. Gradual decompression can be effected by locating the exit orifice above the alfalfa level in the pressure vessel and pumping the ammonia away rather than subjecting it to a rapid pressure drop. The explosive evacuation provides a much more attractive, greener product which is nearly dust free. Explosive evacuation is thus preferred in most cases, particularly if it is to be used as livestock feed because the dust free product is more easily worked with and handled and is more easily pelletized due to its cohesive condition. It is believed that the greener color and dust free nature of the exploded product is due to the explosive discharge propelling protoplasmic material through ruptured cell walls, resulting in particulate cohesion.

Recycling of the ammonia used in the treatment is achieved by recovering it and recompressing it for reuse in treating an additional quantity of crop. The heat generated by recompression of the ammonia can be utilized in a heat exchanger to provide heat for application to the reaction vessel in cases where heat is necessary to supply energy for ammonia vaporization. The ammonia used for treatment of the crop is preferably maintained above atmospheric pressure following evacuation of the vessel in order to minimize the pumping and equipment costs, as will be explained more fully in connection with Example I below. Ammonia recovery is facilitated by the explosive evacuation of the vessel because the exploded product is nearly dust free and is more easily removed from suspension. However, ammonia can also be recovered from the gradually decompressed product without great difficulty. Under normal conditions, less than 5% of the ammonia is retained by the crop, leaving more than 95% for potential recovery and recompression.

The product resulting from pressurized treatment of the crop with ammonia has increased true protein availability as measured by an accepted technique commonly known as TCA precipitation which estimates the quantity of proteinaceous material with molecular weight of approximately 5000 to 10,000. Crude protein is also increased significantly. With mature sun cured alfalfa, which is untreated, the percent of true protein is typically 8% to 9% and the percent of crude protein is typically 12% to 14%. Following the ammonia treatment, typical values are 13% to 15% true protein and 18% to 24% crude protein. It is believed that the treatment effects alteration of the cellulose-lignin configuration in a manner to provide increased availability of true protein from the fibers and from within the cell walls. Without treatment, much of this protein is almost certainly not available to monogastric animals and is likely unavailable to ruminants as well.

The cellulose digestibility, as measured by a 24 hour exposure to cellulase, is increased from about 50% in untreated alfalfa to nearly the theoretical maximum yield of glucose in treated alfalfa. In other words, only about 400 pounds of glucose can be obtained through digestion of one dry ton of untreated mature alfalfa, while 800 pounds of glucose can be produced from treated alfalfa. These results are indicative of the increased cellulosic energy that is available to ruminant animals. It is believed that the greater cellulose digestibility results from alteration of the cellulose (fibers and cell walls) and breaking of the cellulose-lignin bonds which reduces the protection of the cellulose. The enzymatic conversion of the cellulose to glucose is thus enhanced.

The enhancement of the available protein and the increase in the cellulose digestibility of the treated alfalfa makes it valuable as higher energy, mid-protein alfalfa feed for livestock. Alternatively, the protein content of the treated alfalfa can be extracted for use in manufacturing high protein concentrate, and, concurrently, the cellulose can be treated with a cellulase enzyme in a conventional manner to produce glucose which can then be fermented by standard techniques to provide ethyl alcohol (ethanol).

Although the cellulose digestibility and protein content increases are similar for both exploded and gradually decompressed material, the exploded material has a greener color and is nearly free of dust, as previously indicated. The dust free characteristic of the material is retained even at a 4.5% moisture level with a 1/16 inch grind. Untreated ground materials and slowly decompressed materials are dusty. Even though this is a subjective factor, it is nevertheless important in most cases and explosive evacuation is generally preferred for the reasons given previously.

To exemplify the foregoing, the following examples are illustrative of the possible commercial uses of the present invention and the results that can be achieved, but they are not intended to cover all possible applications.

EXAMPLE I

One method of producing an increased protein, highly digestible alfalfa livestock feed involves initially cutting and baling alfalfa or using field wilted hay (30–40% moisture) at full bloom to pod stage. If there is significant lower leaf loss, an earlier stage should be selected to preserve the total protein and cellulose yield. Fewer harvesting operations per year are required in comparison to current practices which are oriented to achieve high protein content per ton of crop. Disease or other pest infestations may require earlier harvest in some cases but is to be avoided if possible. Under most conditions, the bales should be covered to retard deterioration if they are to be stored for winter use.

The alfalfa hay is ground or otherwise reduced to an appropriate size (1/16 inch to ½ inch in most cases) and is fed through an air lock system into an enclosed reactor vessel which is maintained under a pressure of 145 to 165 psig and a temperature of 20° to 30° C. Liquid anhydrous ammonia is injected into the pressure vessel at a rate which effects quick and thorough penetration of the alfalfa for rapid reactions. Typically, one pound of liquid ammonia is applied per pound of dry weight alfalfa. An orifice located beneath the alfalfa level in the reactor vessel allows continuous explosive decompression of the ammonia and treated alfalfa into a primary recovery chamber which is connected with the exit orifice by a tube. The reaction time in this continuous processing system is controlled by the size of the exit orifice and is adjusted to achieve about 30 minutes exposure time of the alfalfa to the ammonia prior to explosive evacuation.

The primary recovery chamber is maintained at a selected pressure which is less than the treatment pressure in the reactor vessel but greater than atmospheric pressure. In the primary recovery chamber, most of the ammonia is recovered and is recompressed to liquid. The recovered ammonia is recycled by compressing it to the treatment pressure and injecting it back into the reactor vessel for treatment of an additional quantity of alfalfa. This recycling of the ammonia not only reduces the ammonia requirements but also reduces the pumping requirements because the recycled ammonia must be compressed only from the primary recovery pressure to the reactor vessel pressure rather than from atmospheric pressure to the reactor vessel pressure.

The alfalfa and retained ammonia are moved from the primary recovery chamber through an air lock system to a secondary recovery chamber which is maintained at a pressure of one atmosphere or less. Depending upon the original moisture content of the hay, varying amounts of heat are applied to the secondary recovery chamber. More moisture in the hay requires less pressure in the secondary chamber and/or more heat to drive off the ammonia. Nearly complete removal of free ammonia from the hay is accomplished in the secondary recovery chamber.

The treated alfalfa is passed from the secondary recovery chamber to a tertiary recovery chamber which operates as conditions warrant. In the case of field wilted alfalfa (30–40% moisture), the tertiary recovery chamber or a similar device is usually required for nearly complete ammonia recovery. Final drying can be accomplished in a rotary drum dehydrator with the exhaust employing a scrubber to prevent traces of ammonia from affecting the environment. The resultant product is a mid-protein alfalfa feed of greater available energy which can be pelleted or handled as meal in the same manner as occurs in present alfalfa processing techniques.

EXAMPLE II

One method of treating alfalfa to prepare a feedstock for protein concentrate manufacturing concurrent with ethanol production involves preparing baled or field wilted alfalfa and feeding it into a pressurized reactor vessel in the manner set forth in Example I. The vessel is maintained at a pressure of 70 to 125 psig and a temperature of 20° to 30° C., and gaseous anhydrous ammonia is injected into the vessel from the vapor phase of a supply tank containing liquid ammonia. The pressure vessel has an exit orifice which opens to a cyclone separator or a similar separation device, but with a pressure reduction only great enough to provide sufficient propulsion from the reactor vessel to the separator. The treated alfalfa is recovered from the separator, while ammonia is pumped from the exhaust and recompressed for reuse. In this case, it is not necessary to recompress the ammonia to liquid but only to provide enough pressure for return of the ammonia to the vapor phase of the ammonia supply tank.

The treated alfalfa is then passed to a second separator of less pressure for removal of more ammonia, especially if the hay originally had 30–40% moisture. The alfalfa is now ready to be used as a feedstock for immediate enzyme hydrolysis of the cellulose to glucose, fermentation of the glucose to ethyl alcohol (ethanol), and extraction of the protein from the alfalfa. The enzyme hydrolysis, fermentation and protein extraction are all carried out conventionally.

As these examples and the results set forth herein indicate, the treatment process of the present invention provides a procedure for obtaining nearly complete alfalfa cellulose digestibility and substantially increased true protein availability, along with an increase in the crude protein. The resulting product can be used as a superior alfalfa livestock feed or, with enzyme hydrolysis, as a high yielding biomass feedstock for ethanol production concurrent with high protein concentrate manufacturing. Economical reuse of the treatment chemical (ammonia) is achieved by recompressing and recycling it. The rapid reaction rates of the process provide the capability for large scale continuous processing operations on a year round, nonseasonal basis.

It is believed that the treatment of alfalfa with ammonia under pressure achieves markedly better results and substantially reduced reaction times than treatment at atmospheric pressure due to the better penetration and mingling of the ammonia that occurs at the higher pressure level. Although the process has been generally described in connection with the treatment of alfalfa, it is not limited to alfalfa. Similar effects can be achieved when the treatment is used with other cellulosic agricultural crops, crop residues or derivatives. Examples of such agricultural crops are those that are commonly stored as hay, such as timothy, coastal bermudagrass, clover and native grasses. Examples of residues are wheat straw, bagasse and alfalfa plants which have had their juice extracted.

Having thus described the invention I claim:

1. A process for enhancing the cellulose digestibility and true protein availability of alfalfa to enhance the alfalfa as a feed for both ruminants and monogastric animals, said process comprising applying ammonia to the alfalfa for a time period less than about one hour at a treatment pressure in the range of about two atmospheres to about forty atmospheres and at a treatment temperature in the range of about 10° C. to about 85° C. to effect alternation of the cellulose-lignin configuration in said alfalfa, thereby increasing the digestibility of the cellulose in the alfalfa and increasing the availability of true protein from the fibers and from within the cell walls of the alfalfa to both ruminants and monogastric animals.

2. A process as set forth in claim 1, wherein the ammonia is applied in a liquid state to the alfalfa in a ratio in the range of about ½ to 2 parts ammonia to one part alfalfa on a weight basis.

3. A process as set forth in claim 1, including the steps of:
   decompressing the alfalfa and ammonia to an intermediate pressure following elapse of said time period, said intermediate pressure being less than the treatment pressure but greater than atmospheric pressure;
   recovering a substantial portion of the ammonia at said intermediate pressure;
   recompressing the recovered ammonia to the treatment pressure for treatment of an additional quantity of alfalfa; and
   decompressing the treated alfalfa and ammonia retained therein to atmospheric pressure.

4. A process for treating alfalfa to enhance the cellulose digestibility and true protein availability to both ruminants and monogastric animals, said process comprising the steps of:
   applying ammonia to the alfalfa for a time period less than about one hour at a treatment pressure greater than atmospheric pressure and at a predetermined temperature to effect alternation of the cellulose-lignin configuration in said alfalfa, thereby increasing the digestibility of the cellulose in the alfalfa and increasing the availability of true protein from the fibers and from within the cell walls of the alfalfa to both ruminants and monogastric animals;
   decompressing the alfalfa and ammonia to an intermediate pressure following elapse of said time period, said intermediate pressure being less than the treatment pressure but greater than atmospheric pressure;
   recovering a substantial portion of the ammonia at said intermediate pressure;
   recompressing the recovered ammonia to the treatment pressure for treatment of an additional quantity of alfalfa; and
   decompressing the alfalfa to atmospheric pressure.

* * * * *